US005635535A

United States Patent [19]
Wagstaff

[11] Patent Number: 5,635,535
[45] Date of Patent: Jun. 3, 1997

[54] METHOD FOR INCREASING BLOOD GLUCOSE LEVELS

[76] Inventor: Robert K. Wagstaff, 1084 Belle Mar, West Des Moines, Iowa 50266

[21] Appl. No.: 628,859

[22] Filed: Apr. 5, 1996

[51] Int. Cl.$^6$ .......................... A61K 31/19; A61K 31/195
[52] U.S. Cl. ............................. 514/557; 514/561
[58] Field of Search ...................... 514/557, 561

[56] References Cited

U.S. PATENT DOCUMENTS

| | | | |
|---|---|---|---|
| 3,867,539 | 2/1975 | Henkin | 424/269 |
| 4,442,113 | 4/1984 | Lassen et al. | 424/267 |
| 4,507,289 | 3/1985 | Coleman et al. | 514/170 |
| 4,666,898 | 5/1987 | Coleman et al. | 514/177 |
| 5,039,698 | 8/1991 | Leung | 514/458 |
| 5,245,046 | 9/1993 | Youngdale et al. | 548/495 |
| 5,340,315 | 8/1994 | Kaye | 434/127 |
| 5,466,547 | 11/1995 | Khoe | 424/439 |

FOREIGN PATENT DOCUMENTS

| | | |
|---|---|---|
| 0129031 | 4/1984 | European Pat. Off. . |
| 0242554 | 4/1984 | European Pat. Off. . |
| 0219276 | 2/1986 | European Pat. Off. . |
| 1381649 | 10/1972 | United Kingdom . |

OTHER PUBLICATIONS

Garrison et al., "The Nutrition Desk Reference" Keats Publishing Co. (CN), 1985, p. 22.

Hume, Michael E.; Ivie, G. Wayne; Courrier, Donald E.; & DeLoach John R.; Fermentation of C-Propionci Acid in 12-Day Old Broiler Chicks; Jan. 20–21, 1992. (p. 23).

Phelps, V.E.; Moran, Jr., E.T.; & Spano, J.S.; Propionic Acid As a Dietary Gluconeogenic Source To Relieve Poult "Starveouts" (p. 27). (1992).

Goff, J.P.; & Horst, R.L.; Calcium Propoinate As A Feed Additive To Combat Ketosis and Subclinical Hypocalcemia; (pp. 1–13). (1995).

Goff, J.P. & Horst, R.L.; Oral Administration of Calcium Salts for Treatment of Hypocalcemia in Cattle; 1993; (pp. 101–108).

*Primary Examiner*—Raymond Henley, III
*Attorney, Agent, or Firm*—Henderson & Sturm

[57] ABSTRACT

A method of increasing blood glucose levels while metabolizing body fat. The method includes the steps of subjecting the individual to conditions where they start to use body fat as an energy source and administering a biologically active gluconeogenic compound to the individual. The preferred compound is calcium propionate; however, other salts of propionic acid, propionic acid itself, and non-essential amino acids may be used. The gluconeogenic compound may be taken by athletes to increase their energy level, and by dieters to reduce or maintain their body weight.

18 Claims, No Drawings

METHOD FOR INCREASING BLOOD GLUCOSE LEVELS

TECHNICAL FIELD

This invention relates to a method of increasing blood glucose levels while metabolizing body fat to increase an individual's energy level.

BACKGROUND ART

The ideal dietary regime for weight reduction is to consume about two-thirds of the food that it normally takes to keep the body in weight balance. The other one-third of the energy will come from body fat stores.

If an individual is to loose weight, they must reduce the mount of food it normally takes to maintain their body weight. All of the food eaten will be absorbed and will be metabolized by the body. The individual should continue to eat a balanced low-fat diet. During a weight reduction program a woman of normal weight should consume about 1,100 calories and a man of normal weight about 1,600 calories per day. Such a program is designed for a weight loss of about two (2) pounds of body weight per week.

When a person reduces food intake below that needed to support the energy requirements of the body, the liver begins to metabolize body fat as a source of energy. When body fat is metabolized in the absence of a proper balance of carbohydrate, the result is the formation of ketones, which result in ketosis.

In ketosis, the body acts to remove the ketones from the body through the lungs, bile and urine. The dieting person can taste the ketones and also smell them coming from their breath. Ketones can be toxic to the body if present in high amounts for an extended period of time.

Ketone production does not occur when there is a sufficient amount of proper carbohydrate present to "balance with" the fat that is being metabolized. To properly metabolize body fat, the liver requires some amount of carbohydrate to completely utilize this fat. When a balanced diet is eaten, ketones are not produced because the body can completely metabolize both the fat and the carbohydrate into carbon dioxide and water.

When the body is in metabolic balance the "hunger" desire is not present. During dieting the body will burn up the dietary carbohydrate and then start to use body fat. At this point the body is "notified" that it needs more food, so the dieter will feel hungry.

Animal trials have been done in the past few years that yielded unexpected and little-noted results.

Propionic acid was given to chickens for the purpose of trying to control salmonella in the digestive system. To the surprise of the researchers, the propionic acid did not stay in the digestive system but was rapidly absorbed into the blood stream before it reached the small intestines [FERMENTATION OF $^{14}$C-PROPIONIC ACID IN 12-DAY OLD BROILER CHICKS. Michael E. Hume*, G. Wayne Ivie, Donald E. Corrier, and John R. DeLoach. U.S. Department of Agriculture, Agricultural Research Service, Rt. 5, Box 810, College Station, TX]. This finding was a complete surprise to poultry scientists.

Propionic acid was given to turkey poults to overcome early mortality. This data shows that the gluconeogenic property of propionic acid helped the turkey poults to better utilize the fat of the yolk sac. Turkeys that were small and weak were able to maintain life in the presence of propionic acid [PROPIONIC ACID AS A DIETARY GLUCONEO- GENIC SOURCE TO RELIEVE POULT "STARVEOUTS". V. E. Phelps*, E. T. Moran, Jr., and J. S. Spano, Poultry Science Dept. and Pathobiology Dept. Auburn University, AL 36849–5416].

Calcium propionate was used to cure mild fever and ketosis in diary cows. This confirms the assumption that the gluconeogenic properties of calcium propimate helped the diary cow to better utilize body fat without the production of ketones during the onset of milk production. At this time the cow needs more energy for milk production than she can obtain via food, so she utilizes body fat stores [CALCIUM PROPIONATE AS A FEED ADDITIVE TO COMBAT KETOSIS AND SUBCLINICAL HYPOCALCEMIA. J. P. Goff(Pdncipal Investigator) and R. L. Horst, Metabolic Diseases and Immunology Unit USDA, Agricultural Research Service, National Animal Disease Center, Ames, Iowa 50010–0070; ORAL ADMINISTRATION OF CALCIUM SALTS FOR TREATMENT OF HYPOCALCEMIA IN CATTLE. J. P. Coifand R. L. Horst, USDA, Agricultural Research Service, National Animal Disease Center, Metabolic Disease and Immunology Research Unit, Ames, Iowa 50010–0070].

U.S. Pat. No. 5,039,698 to Leung discloses a method of weight reduction using pantothenic acid as the active ingredient. The mode of action of pantothenic acid to reduce weight is by pantothenic acid acting to form Coenzyme A. The presence of Coenzyme A then causes the body to burn various metabolites to control weight and ketosis. One major disadvantage of this method is that pantothenic acid is not absorbed into the blood stream via the stomach wall.

Although calcium propionate has been used in human foods as a mold control agent, there is no suggestion leading scientist to conclude that calcium propionate could be used to help control weight.

DISCLOSURE OF THE INVENTION

The present invention provides a method of increasing blood glucose levels while metabolizing body fat. The method includes the steps of subjecting the individual to conditions where the body starts to use stored fat as an energy source and then, administering a biologically active gluconeogenic compound to the individual. The preferred compound is calcium propionate; however, other salts of propionic acid, propionic acid itself, and non-essential amino acids may be used. The gluconeogenic compound may be taken by athletes to increase their energy level, and by dieters to reduce or maintain their body weight.

An object of the present invention is the provision of an improved method of increasing blood glucose levels while metabolizing body fat.

Another object is to provide a method of increasing blood glucose levels to enhance the energy level of an individual.

A further object of the invention is the provision of method of increasing blood glucose levels to prevent ketosis while metabolizing body fat.

Still another object is to provide a method of increasing blood glucose levels to reduce the feeling of hunger in an individual subjected to a reduced caloric intake.

These and other attributes of the invention will become more clear upon a thorough study of the following description of the best mode for carrying out the invention, particularly when reviewed in conjunction with the examples.

BEST MODE FOR CARRYING OUT THE INVENTION

The following examples are illustrative of the best mode for carrying out the invention. They are obviously not to be construed as limitative of the invention since various other embodiments can readily be evolved in view of the teachings provided herein.

EXAMPLE 1

The method of the present invention includes the ingestion of calcium propionate taken as part of a weight reduction program. The calcium propionate is a source of propionic acid which is gluconeogenic. In the preferred embodiment, pills are supplied to the dieter and each pill contains 350 mg. calcium propionate. One or two pills, as needed to control hunger, are taken two to four times a day, 15 to 30 minutes before mealtime or in the evening.

The method of the present invention provides a compound that is gluconeogenic. Gluconeogenic compounds are organic compounds that will enable the liver to produce some glucose, even when there is no dietary glucose present. The preferred active gluconeogenic component is calcium propionate. When calcium propionate is taken into the stomach, the stomach acid converts it to propionic acid which is rapidly absorbed into the blood stream, then transferred to the liver where it is converted into glucose. The glucose that is produced balances with the body fat that is being utilized by the liver. This eliminates the production of ketones and prevents ketosis during dieting. The unique ability of propionic acid to be absorbed via the stomach lining rather than to pass into the small intestine to be absorbed is one of the key reasons why the present invention works so well. This ability insures that the propionic acid reaches the liver within minutes after the calcium propionate pill is taken.

Therefore, the present invention enables the body to utilize body fat for energy without producing the toxic ketone compounds. It is noteworthy to mention that in the presence of propionic acid the body fat is completely metabolized. Weight loss will now be slower because body fat is now completely metabolized to carbon dioxide and water, rather than partly metabolized into ketones. Propionic acid will rapidly stimulate glucose production and bring the body back into metabolic balance so the hungry feeling goes away. In practice, this can occur within 10 to 20 minutes after ingesting calcium propionate.

Water is the most important nutrient needed by the body. It is essential that a dieter take at least one eight ounce glass of fluid every time they ingest a diet pill. The body cannot function without sufficient water to aid metabolism and to get rid of the byproducts of metabolism. Insufficient water consumption during dieting can be very harmful and will cause headaches. During the dieting period, the dieter needs to consume at least eight glasses of fluid (eight ounce size) per day. This dietary plan should not be undertaken without drinking enough water and/or liquids.

When dieting, an individual should consume about two-thirds of the energy that is normally required to sustain their body weight. This decrease in food intake will also lower intake of vitamins and minerals which are required for normal body function. These vitamins and minerals must now be provided in the form of a supplement. Vitamins and minerals are needed for normal body function and are still needed while burning body fat as energy. These must be ingested in the form of supplements during a weight reduction program.

While dieting, the individual should continue to exercise as much as they feel like. It is suggested that the dieter walk at least one-half hour per day or undertake the equivalent amount of some other exercise. This exercise is very beneficial because the individual will notice an improvement in how they feel about themselves as they loose weight. Also, dieters will generally experience an increase in their desire for activity.

There are no side affects of taking the diet pills containing calcium propionate; however, because propionic acid is rapidly absorbed into the blood stream and the blood stream is associated with the taste buds in the mouth, the dieter may notice a "soapy" mouth taste. This mouth taste is not harmful nor is it ketosis, but it may be present as long as the dieter takes the diet pills.

Propionic acid has been classified as GRAS (Generally Recognized As Safe) by the FDA. Propionic acid is a normal metabolite of the body. Propionic acid is a commonly used product in foods. For example, it is used in various foods such as breads, cakes, tacos, etc., as a mold inhibitor. It is not a drug and it's gluconeogenic action will be eliminated when sufficient food is consumed to satisfy the body's need for a balanced energy source. Propionic acid will not increase body metabolism rate nor will it improve the food value of normal food. It only works when the individual eats less food than the body needs for body maintenance and calls upon body fat stores for energy.

The following are suggested materials to be provided to an individual using the weight reduction regime of the present invention.

1. THE WEIGHT REDUCTION PROGRAM IN SUMMARY

* Weigh yourself. Start a weight chart to record your weight loss each week.
* Start by taking one or two pills (with liquid) the morning of the first day. Eat a very light breakfast or no breakfast if you like. Take a vitamin/mineral pill.
* Take another one or two pills about 11:30 A.M. (with liquid). Eat a very light lunch at 12:00 P.M.
* Take another one or two pills about 4:30 P.M. (with liquid). Eat a very light dinner at about 6:00 P.M.
* If hungry at 8–9 P.M., take another pill (with liquid). Eat a very light snack.
* Drink a liquid between meals in the morning and in the afternoon and after dinner in the evening.
* Exercise 30 minutes sometime during the day.
* Repeat this regime each day of your diet.
* You may choose to miss a meal. This is okay if you want to do this provided you take your diet pill.
* After reaching your ideal weight, then start on the maintenance weight program.

| 2. YOUR WEIGHT CHART | | | |
|---|---|---|---|
| Week Ending | Goal Weight | Actual Weight | Pounds Lost |
| | | | |
| | | | |
| | | | |
| | | | |

3. THE MAINTENANCE PROGRAM

After you reach your desired weight reduction goal it is important to maintain your idea weight. If you allow your weight to go back up, you have lost the benefit of your efforts to keep your body at the proper weight. During your weight reduction program, you will have programmed yourself to eat smaller portions of food. By continuing to eat small portions of food after you reach your weight goal, you should now be able to maintain your body weight. The Maintenance Program is designed to help you maintain your ideal weight.

It is very easy to maintain your ideal weight. The process is as follows:
1. Weigh yourself regularly, at least weekly.
2. Should your weight increase five pounds above your ideal weight, start back on the weight reduction program.
3. You should be able to loose the five extra pounds in about two weeks.
4. By keeping your weight within five pounds of your ideal weight, you will be able to always enjoy the benefits of being at your ideal weight.

4. PARTING COMMENTS:

Remember, you cannot loose weight unless you actually eat less.

If you break your dietary regime one day, do not be discouraged, just start again the next day. Be assured that you will benefit your body for every day that you are on the program. You can be sure that this program will result in weight loss.

5. SUGGESTED LUTEIN SUPPLEMENT
I care
60 Softgels
NATURES LIFE
Garden Grove, California

| Each capsule contains: | | % U.S. RDA |
|---|---|---|
| Luetin | 6 mg. | * |
| Beta Carotene | 3 mg. | * |
| Zeazanthin | 435 mcg. | * |
| Alpha Carotene | 96 mcg. | * |
| Caryptoxanthin | 22 mcg. | * |
| Zinc | 40 mg. | 267 |
| Copper | 2.5 mg. | 125 |

This product is available at most health food stores.

6. SUGGESTED VITAMIN/MINERAL SUPPLEMENT
MUTRI-MEGA
super potency vitamin and mineral supplement
120 softgels
AMERICAN HEALTH
Bohemia, New York

| Two (2) Softgels Supply: | | % U.S. RDA |
|---|---|---|
| Vitamin A | 10,000 I.U. | 200 |
| Vitamin D | 400 I.U. | 100 |
| Vitamin C | 300 mg. | 500 |
| Rutin | 10 mg. | ** |
| Vitamin E | 300 I.U. | 1000 |
| Vitamin B-1 | 50 mg. | 3333 |
| Vitamin B-2 | 50 mg. | 2940 |
| Vitamin B-6 | 50 mg. | 2500 |
| Vitamin B-12 | 50 mg. | 833 |
| Pantothenic Acid | 50 mg. | 500 |
| Bioflavonoids | 30 mg. | ** |
| Para Aminobenzoic Acid | 50 mg. | *** |
| Niacinamide | 50 mg. | 250 |
| Folic Acid | 400 mcg. | 100 |
| Biotin | 50 mcg. | 16.6 |
| Royal Jelly | 5 mg. | ** |
| Choline | 50 mg. | ** |
| Inositol | 50 mcg. | ** |

6. SUGGESTED VITAMIN/MINERAL SUPPLEMENT
-continued
MUTRI-MEGA
super potency vitamin and mineral supplement
120 softgels
AMERICAN HEALTH
Bohemia, New York

| Two (2) Softgels Supply: | | % U.S. RDA |
|---|---|---|
| Garlic Oil | 2 mcg. | ** |
| Lecithin | 80 mg. | *** |
| Calcium | 200 mg. | 20 |
| Phosphorus | 50 mg. | 5 |
| Iron | 18 mg. | 100 |
| Octacosanol | 10 mcg. | ** |
| Copper | 2 mcg. | 100 |
| Iodine | 150 mcg. | 100 |
| RNA | 2 mg. | ** |
| DNA | 2 mg. | ** |
| Magnesium | 50 mg. | 12.5 |
| Zinc | 15 mg. | 100 |
| Manganese | 30 mg. | ** |
| Potassium | 30 mg. | ** |
| Chromium Picolinate | 25 mcg. | *** |
| Co-Q-10 | 100 mcg. | * |
| Boron | 1 mg. | * |
| Selenium | 25 mcg. | ** |

*No U.S. Recommended Daily Allowance established.
**Need in human nutrition established, but no U.S. RDA established.
***No nutritional value claimed.
DIRECTIONS: Take two (2) softgels daily, as a dietary supplement. For improved utilization, take one (1) at breakfast and one (1) at dinner.

This product is available at most health foods stores.

7. SUGGESTED WEIGHTS FOR ADULTS
(Range Includes Men and Women)
(According to the U.S. Dietary Guidelines)

| HEIGHT | WEIGHT IN POUNDS (Without Clothes) | |
|---|---|---|
| (Without Shoes) | 19–34 Years | 35 Years and Over |
| 5'0" | 97–128 | 108–138 |
| 5'1" | 101–132 | 111–143 |
| 5'2" | 104–137 | 115–148 |
| 5'3" | 107–141 | 119–152 |
| 5'4" | 111–146 | 122–157 |
| 5'5" | 114–150 | 126–162 |
| 5'6" | 118–155 | 130–167 |
| 5'7" | 121–160 | 134–172 |
| 5'8" | 125–164 | 138–178 |
| 5'9" | 129–169 | 142–183 |
| 5'10" | 132–174 | 146–188 |
| 5'11" | 136–179 | 151–194 |
| 6'0" | 140–184 | 155–199 |
| 6'1" | 144–189 | 159–205 |
| 6'2" | 148–195 | 164–210 |
| 6'3" | 152–200 | 168–216 |
| 6'4" | 156–205 | 173–222 |
| 6'5" | 160–210 | 177–228 |
| 6'6" | 164–216 | 182–234 |

EXAMPLE 2

The following results have been documented using diet pills, each containing 350 mg. calcium propionate.
Person Number 1:
  Daily Regime:
  Breakfast: Drink 12 ounces of orange drink with a diet pill, one vitamin/mineral pill.
  Mid-morning: Drink 12 ounces of water.
  11:30 A.M.: Take a diet pill with water.
  12:00 P.M.: Each a dinner salad or small low-fat sandwich. Drink 12 ounces of liquid:

2:30 P.M.: Drink a 12 ounce diet drink.
4:30 P.M.: Take a diet pill with water.
6:00 P.M.: Eat a light dinner of meat and vegetable with 12 ounces of liquid.
8:00 P.M.: Take a diet pill with 12 ounces of liquid.
9:00 P.M.: Have a light snack. Sometimes even ice cream. Drink liquid.

| Weight loss chart: | | |
|---|---|---|
| Week | Pounds Lost | Total Pounds Lost |
| 1 | 5 | 5 |
| 2 | 5 | 10 |
| 3 | 2 | 12 |
| 4 | 3 | 15 |
| 5 | 2 | 17 |
| 6 | 0 | 17 (Holiday Season) |
| 7 | 2 | 19 |

Person Number 2:
Take two pills before breakfast with liquid.
Take two pills before dinner with liquid.
Take one pill in the evening.
Comments:
1. Pills helped Person Number 2 from feeling hungry.
2. Person Number 2 watched food intake so that they ate less food.
Weight Loss: Twenty pounds weight lost in five weeks.

EXAMPLE 3

Over 30 other people have taken these calcium propionate diet pills. All have reported that the pills reduced hunger.

The following people have reported their experience:

Person A. Lost 29 pounds in 12 weeks time. Took four, 350 mg. pills per day. One prior to each meal and one in the evening.

Person B. Lost 16 pounds in 6 weeks time. Took four, 350 mg. pills per day. One prior to each meal and one in the evening.

Person C. Lost 5 pounds in 4 weeks time. Took two, 350 mg. pills per day. One in the morning and one prior to lunch.

Person D. Lost 12 pounds in 2 weeks. Took five, 350 mg. pills per day. One in the morning, one at noon, two before dinner, and one in the evening.

Person E. As a long distance runner, this person took four, 350 mg. pills (175 mg. calcium propionate, 175 mg. alanine) each day while running ten miles. He has reported feeling no ill affects. This runner is continuing to determine the number of pills to take and the best time to take the pills for optimum results.

EXAMPLE 4

Propionic acid, salts of propionic acid, or alanine can be used to improve the energy level of people who participate in sports. After prolonged exercise by an individual, such as a long distance runner or a basketball player, the individual's body begins to use fat as a source of energy. When that occurs, administering propionic acid or salts of propionic acid will increase the glucose level in the blood. This increase in glucose level will provide "extra" energy for the athlete.

Collected blood samples have been tested for glucose levels and show that the blood glucose increases during prolonged exercise. Athletes can ingest salts of propionic acid or alanine after a certain exercise time to renew their energy levels. This would be very helpful for a basketball player during the second half of the game, for long distance runners, for people who ride long distances on a bicycle, etc.

EXAMPLE 5

Blood and Urine Data On Calcium Propionate Administration

1. BLOOD GLUCOSE TEST NUMBER 1:

Effect of taking various amounts of calcium propionate on the blood glucose level. Blood glucose determined by using the CHEMSTRIP bG Strips as read in the Accu-Chek II system. This is the system most used by people who need to check their blood glucose at home.

| Date: | Time: | Results: |
|---|---|---|
| Day 1 | 6:00 P.M. | Blood glucose 92 mg/dl |
| Day 2 | 6:20 A.M. | Blood glucose 120 mg/dl |

Blood glucose taken after 35 minutes walking on treadmill. This patient ate no breakfast this day. Waited until he began to feel hungry. Measured blood glucose.

10:30 A.M. Blood glucose 73 mg/dL

At 10:35 A.M. took one pill containing 350 mg. of calcium propionate.

11:10 A.M. Blood glucose 81 mg/dL

Hunger had subsided. Notice that blood glucose had risen to 81 mg/dL in about 35 minutes. This is an increase of 11 percent glucose.

2. BLOOD GLUCOSE TEST NUMBER 2:

This patient fasted from 12:30 P.M. on day one to 8:30 A.M. on day two, a period of 20 hours. The blood glucose was taken and then the patient took one pill containing 350 mg. of calcium propionate and waited 15 minutes. Blood glucose was then taken and recorded. At 15 minutes the patient took a second pill. At 30 minutes the blood glucose was taken and the patient then took a third pill. Blood glucose was then taken at 45 and at 60 minutes. Table 1 summarizes the data from this test.

TABLE 1

| Time of Day | (Min.) | Pill Taken | Blood Glucose mg % | Change From Beginning Level |
|---|---|---|---|---|
| 8:30 A.M. | (0) | Pill 1 | 55 | — |
| 8:45 A.M. | (15) | Pill 2 | 67 | 122 |
| 9:00 A.M. | (30) | Pill 3 | 72 | 131 |
| 9:15 A.M. | (45) | None | 74 | 135 |
| 9:30 A.M. | (60) | None | 73 | 133 |

The data in Table I illustrates that the blood glucose rose to a high of 135 percent of the beginning level at 45 minutes after taking the first pill. This demonstrates the effect of propionic acid as a gluconeogenic compound in humans. This increase in blood glucose occurs within 15 minutes after taking the first pill.

3. URINE KETOSIS TEST:

This test shows the effect of fasting for 20 hours on the ketosis level in the urine and the effect of taking calcium propionate on ketone levels in the urine.

The patient did not eat food from 12:00 P.M. (Noon) on day one until 8:00 A.M. on day two, a period of 20 hours.

At 8:00 A.M. on day two, a sample of urine was tested for ketosis. Ketostix (Miles Laboratories) were used to measure the level of ketosis. Urine showed between 5 and 10 mg/dL ketone in the urine.

At 8:10 A.M., the patient took one pill containing 350 mg. of calcium propionate.

At 9:15 A.M. a urine sample was taken and measured for ketones. No ketones were found to be in the urine as tested by the Ketostix method.

The pill acted to reduce the ketone level in the urine from a range of about 5–10 mg. to 0 mg. in about one hour. No food was eaten by the patient during this time period.

Propionic acid and calcium propionate are preferred active ingredients used in the method of the present invention. It is important to understand that any salt of propionic acid that reaches the stomach would be immediately converted to propionic acid because of the low pH of the stomach. Within the context of this disclosure, propionic acid is the active ingredient within the individual's body.

Alanine is not immediately convened to propionic acid when it reaches the stomach because it is already in acid form and also cannot be readily deamintated within the stomach. In order to be gluconeogenic it must first be deaminated which probably occurs in the liver after having been absorbed via the small intestine. This may explain the relatively longer delay in controlling hunger when alanine is administered to an individual.

The present invention was developed using the various different observations that have been made by different scientists who used propionic acid or salts of propionic acid in different animals and poultry for various purposes. The genesis of the present invention came from Applicant's conclusion based on available information. However, the present invention was not taught or suggested by the available information from any source considered individually or in combination with other sources.

It has not been taught or suggested that propionic acid or any salt of propionic acid could be used in humans for weight control. Even though propionic acid has been used in human foods it has not been used to increase blood level glucose, increase the energy level of an individual, or to assist in weight reduction and/or weight maintenance programs.

The present invention has the following key features:

Applicant has proven by actual ingestion that calcium propionate does act in the human body as a gluconeogenic agent.

Applicant has proven by testing his urine that it does prevent the production of ketones and ketosis when the body is burning stored fat. When there are no ketones present during dieting then there will not be headaches.

Applicant has proven that the use of calcium propionate will prevent a person from having hunger feelings when fasting or dieting. Further, it was concluded that this action occurs very rapidly in the human body because the propionate portion of calcium propionate is rapidly absorbed into the blood stream via the stomach wall.

Applicant has demonstrated that calcium propionate will help the body to maintain normal glucose levels during dieting. These normal glucose levels will prevent a person from feeling "tired and restless" because they will have normal levels of energy during this dieting period. Normal glucose levels during fasting will also help prevent headaches from occurring.

Applicant has confirmed his personal observations by making available to other people, free of charge, capsules of calcium propionate, capsules of alanine, or alanine with calcium propionate. They have also confirmed that such pills do help to control hunger, do help them to loose weight, and do this without energy loss or headaches.

Applicant has determined that this action of calcium propionate can be accomplished by taking from two to four 350 mg. capsules of calcium propionate per day for a total daily dosage of about 0.7 to 1.4 grams.

Calcium propionate is but one source of gluconegenic compounds that could be used to control weight. Others include sodium propionate, ammonium propionate, magnesium propionate, potassium propionate, zinc propionate, copper propionate, and other non-toxic salts.

There are several amino acids that are also gluconeogenic such as alanine and other non-essential amino acids.

The real advantage to calcium propionate is that it is easily ingested and readily adsorbed by the human body. It is a powder that can be taken without any harm. Calcium is also a nutrient that can be readily used by the human body. The key to this success is that the calcium propionate is rapidly ionized when it reaches the very low acid condition in the stomach. Upon being ionized, it will readily pass through the stomach lining into the blood stream and then be carded to the liver where it is a very active gluconeogenic agent. It is the most desirable of the propionate salts.

The following key factors concerning the use of propionic acid, or the salts of propionic acid, distinguish the present invention over the prior art. Propionic acid is the active ingredient, which is converted to glucose. Propionic acid is also a co-factor that assists the stored fats in the body to metabolize into glucose rather than ketones, thus preventing ketosis. Propionic acid is not a derivative of pantothenic acid, although pantothenic acid contains a propionic acid radical as part of its structure. Propionic acid has the unique ability to be absorbed into the blood stream via the stomach wall. Pantothenic acid is not known to be absorbed via the stomach wall. Propionic acid is directly gluconeogenic. Pantothenic acid is indirectly involved in the gluconeogenic process when gluconeogenic metabolites are present. Less than five grams of propionic acid, salts of propionic acid, or alanine are required per day. More than five grams of pantothenic acid are needed for efficiency. Propionic acid or salts of propionic acid are given primarily orally but could be given intravenously or rectally.

While only certain preferred embodiments of this invention have been shown and described by way of illustration, many modifications will occur to those skilled in the art and it is, therefore, desired that it be understood that it is intended herein to cover all such modifications that fall within the true spirit and scope of this invention.

I claim:

1. A method for increasing glucose levels in an individual's blood, comprising:

subjecting the individual to conditions where the individual starts to use body fat as a source of energy; and administering to the individual an effective amount of a biologically active ingredient selected from the group consisting of propionic acid, salts of propionic add, and non-essential amino acids.

2. The method of claim 1 wherein the individual is subjected to physical exercise to initiate the use of body fat as a source of energy.

3. The method of claim 1 wherein the individual is subjected to a reduced caloric intake to initiate the use of body fat as a source of energy.

4. The method of claim 2 wherein the individual is subjected to a reduced caloric intake to initiate the use of body fat as a source of energy.

5. The method of claim 1 wherein the active ingredient is calcium propionate.

6. The method of claim 1 wherein the active ingredient is sodium propionate.

7. The method of claim 1 wherein the active ingredient is alanine.

8. The method of claim 1 wherein the active ingredient is administered in a daily dosage &from about 0.1 to about 5.0 grams per day.

9. The method of claim 8 wherein the active ingredient is administered in a daily dosage of from about 0.7 to about 2.8 grams per day.

10. The method of claim 8 wherein the active ingredient is calcium propionate.

11. A body weight reducing regime for an individual, comprising:
- administering to the individual an effective amount of a biologically active ingredient selected from the group consisting of calcium propionate and sodium propionate; and
- reducing the caloric intake of the individual to a level below that required to maintain the body weight of the individual.

12. The regime of claim 11 wherein the active ingredient is administered in a daily dosage of from about 0.1 to about 5.0 grams per day.

13. The regime of claim 12 wherein the active ingredient is administered in a daily dosage of from about 0.7 to about 2.8 grams per day.

14. The regime of claim 12 wherein the active ingredient is calcium propionate.

15. A body weight maintenance regime for an individual, comprising:
- administering to the individual an effective amount of a biologically active ingredient selected from the group consisting of calcium propionate and sodium propionate; and
- controlling the caloric intake of the individual at a level no greater than that required to maintain the body weight of the individual.

16. The regime of claim 15 wherein the active ingredient is administered in a daily dosage of from about 0.1 to about 5.0 grams per day.

17. The method of claim 16 wherein the active ingredient is administered in a daily dosage of from about 0.7 to about 2.8 grams per day.

18. The method of claim 16 wherein the active ingredient is calcium propionate.

* * * * *